United States Patent
Lee (10) Patent No.: US 10,627,511 B2
(45) Date of Patent: Apr. 21, 2020

(54) ULTRASONIC TRANSDUCER HAVING FLEXIBLE PRINTED CIRCUIT BOARD WITH THICK METAL LAYER AND MANUFACTURING METHOD THEREOF

(71) Applicant: ALPINION MEDICAL SYSTEMS CO., LTD., Seoul (KR)

(72) Inventor: Won-Seok Lee, Daegu (KR)

(73) Assignee: Alpinion Medical Systems Co., Ltd., Seoul (KR)

( * ) Notice: Subject to any disclaimer, the term of this patent is extended or adjusted under 35 U.S.C. 154(b) by 365 days.

(21) Appl. No.: 15/526,108

(22) PCT Filed: Dec. 22, 2014

(86) PCT No.: PCT/KR2014/012636
§ 371 (c)(1),
(2) Date: May 11, 2017

(87) PCT Pub. No.: WO2016/104820
PCT Pub. Date: Jun. 30, 2016

(65) Prior Publication Data
US 2017/0307756 A1    Oct. 26, 2017

(51) Int. Cl.
*B06B 1/06* (2006.01)
*G01S 15/89* (2006.01)
(Continued)

(52) U.S. Cl.
CPC ........ *G01S 15/8956* (2013.01); *A61B 8/4494* (2013.01); *B06B 1/0644* (2013.01);
(Continued)

(58) Field of Classification Search
None
See application file for complete search history.

(56) References Cited

U.S. PATENT DOCUMENTS 4,806,937 A * 2/1989 Peil .................. G01S 7/282
                                                342/175
4,870,421 A * 9/1989 Peil .................. G05F 1/575
                                                342/175
(Continued)

FOREIGN PATENT DOCUMENTS

CN    102598330 A    7/2012
CN    103380352 A    10/2013
(Continued)

OTHER PUBLICATIONS

Chinese Patent Office, 201480083558.9, Related U.S. Appl. No. 15/526,108, First Office Action, English Translation, dated 2014. (Year: 2014).*

(Continued)

*Primary Examiner* — Hovhannes Baghdasaryan
*Assistant Examiner* — Jonathan D Armstrong
(74) *Attorney, Agent, or Firm* — NSIP Law (57) ABSTRACT

An ultrasonic transducer having a flexible printed circuit board with a thick metal layer and a manufacturing method thereof are disclosed. The ultrasonic transducer, according to an embodiment of the present invention, comprises: an active element that generates an ultrasonic signal, wherein the active element has a thickness of ¼λ or less at the center frequency of the generated ultrasonic signal; and a flexible printed circuit board that includes a metal layer with a predetermined thickness, which is formed on one surface of the active element and is electrically connected to the active element, wherein the metal layer blocks ultrasonic waves that propagate in an opposite direction to a predetermined travel path of the ultrasonic waves.

9 Claims, 7 Drawing Sheets

(51) Int. Cl.
  *H04R 17/00* (2006.01)
  *H04R 31/00* (2006.01)
  *G01S 7/52* (2006.01)
  *A61B 8/00* (2006.01)

(52) U.S. Cl.
  CPC ....... *G01S 7/52079* (2013.01); *G01S 15/8911* (2013.01); *G01S 15/8915* (2013.01); *H04R 17/00* (2013.01); *H04R 31/00* (2013.01)

(56) References Cited

U.S. PATENT DOCUMENTS

| | | | | |
|---|---|---|---|---|
| 5,377,166 | A * | 12/1994 | Kuhn | G10K 11/008 367/135 |
| 5,530,680 | A * | 6/1996 | Whitehurst | G01S 3/808 367/99 |
| 5,553,035 | A | 9/1996 | Seyed-Bolorforosh et al. | |
| 7,905,007 | B2 * | 3/2011 | Calisti | B06B 1/0618 29/25.35 |
| 8,836,203 | B2 * | 9/2014 | Nobles | B06B 1/0622 310/327 |
| 9,180,490 | B2 * | 11/2015 | Tai | B06B 1/0622 |
| 10,310,061 | B2 * | 6/2019 | Angelsen | B32B 5/16 |
| 10,326,072 | B2 * | 6/2019 | Toda | H01L 41/22 |
| 2002/0156379 | A1 | 10/2002 | Angelsen et al. | |
| 2008/0125658 | A1 * | 5/2008 | Lee | A61B 8/12 600/459 |
| 2009/0048519 | A1 | 2/2009 | Hossack et al. | |
| 2010/0237746 | A1 * | 9/2010 | Calisti | B06B 1/0618 310/334 |
| 2011/0050039 | A1 * | 3/2011 | Toda | B06B 1/0622 310/327 |
| 2011/0125148 | A1 * | 5/2011 | Turner | A61B 18/1815 606/33 |
| 2011/0178407 | A1 * | 7/2011 | Lu | A61B 8/4281 600/459 |
| 2013/0169818 | A1 | 7/2013 | Ko et al. | |
| 2013/0241356 | A1 | 9/2013 | Kim et al. | |
| 2013/0257226 | A1 * | 10/2013 | Nobles | B06B 1/0622 310/327 |
| 2013/0315035 | A1 * | 11/2013 | Tai | B06B 1/0622 367/140 |
| 2016/0332198 | A1 * | 11/2016 | Toda | H01L 41/22 |
| 2016/0363656 | A1 * | 12/2016 | Angelsen | G01S 7/521 |
| 2018/0169701 | A1 * | 6/2018 | Daloz | B06B 1/0644 |
| 2018/0175278 | A1 * | 6/2018 | Daloz | B06B 1/0644 |
| 2018/0290175 | A1 * | 10/2018 | Palchetti | A61B 8/4483 |

FOREIGN PATENT DOCUMENTS

| | | |
|---|---|---|
| JP | 2000-131298 A | 5/2000 |
| JP | 2004-518319 A | 6/2004 |
| JP | 2012-034159 A | 2/2012 |
| KR | 10-1195671 B1 | 10/2012 |
| KR | 10-2013-0078972 A | 7/2013 |
| KR | 10-2013-0104202 A | 9/2013 |
| KR | 10-2014-0031533 A | 3/2014 |
| WO | WO 2011/028430 A1 | 3/2011 |
| WO | WO 2012/113401 A1 | 8/2012 |

OTHER PUBLICATIONS

International Search Report dated Sep. 17, 2015 in International Patent Application No. PCT/KR2014/012636 (5 pages, with English translation).

Chinese Office Action dated Nov. 14, 2019 in counterpart Chinese Patent Application No. 201480083558.9 (6 pages in Chinese).

* cited by examiner

ULTRASONIC TRANSDUCER HAVING FLEXIBLE PRINTED CIRCUIT BOARD WITH THICK METAL LAYER AND MANUFACTURING METHOD THEREOF

CROSS-REFERENCE TO RELATED APPLICATIONS

This application is a U.S. National Stage Application of International Application No. PCT/KR2014/012636, filed on Dec. 22, 2014.

TECHNICAL FIELD

The present invention relates to an ultrasonic transducer which obtains internal image information of a subject using ultrasonic waves.

BACKGROUND ART

An ultrasonic diagnostic apparatus is an apparatus which images the internal tissue of a subject with a reflected ultrasonic signal by emitting an ultrasonic signal to the subject. The ultrasonic diagnostic apparatus transmits an ultrasonic signal to a diagnostic region of a subject to be examined and subsequently receives an ultrasonic signal reflected from a boundary between the internal tissues of the subject having different acoustic impedances, thereby obtaining image information of the diagnostic region.

The ultrasonic diagnostic apparatus includes an ultrasonic transducer to transmit an ultrasonic signal to a subject and receive an ultrasonic signal reflected from the subject. The ultrasonic transducer includes an active element, a matching layer, and a backing layer.

Technical Problem

An ultrasonic transducer having a flexible printed circuit board with a thick metal layer in order to improve the sensitivity and bandwidth, and a manufacturing method thereof are provided according to embodiments.

Technical Solution

The present invention provides an ultrasonic transducer including: an active element configured to generate an ultrasonic signal and have a thickness of ¼ wavelength or less at a center frequency of the generated ultrasonic signal; and a flexible printed circuit board having a metal layer which is formed on one surface of the active element, is electrically connected to the active element and has a predetermined thickness to block ultrasonic waves that propagate in a direction opposite to a predetermined travel path of the ultrasonic waves.

The thickness of the metal layer may be ⅔ wavelength or more at the center frequency of the ultrasonic signal.

The metal layer of the flexible printed circuit board may be formed on a rear surface of the active element and applies an electrical signal to the active element, the active element may generate the ultrasonic signal by an electrical signal applied from the metal layer and transmit the ultrasonic signal, and an interface between the metal layer and the active element may act as a node due to the thickness of the metal layer so that the ultrasonic signal is blocked from propagating in a direction of a backing layer formed on a rear surface of the flexible printed circuit board and the ultrasonic signal propagates only in the direction of the predetermined travel path of ultrasonic waves, and thereby sensitivity and bandwidth of the ultrasonic transducer are increased.

The metal layer of the flexible printed circuit board may be deposited on one surface of the active element to a predetermined thickness.

The metal layer of the flexible printed circuit board may be deposited as a thick film.

An acoustic impedance and thermal conductivity of the metal layer may be controlled by selecting or mixing at least one or more metal raw materials.

The metal layer may be formed of one of copper, gold, silver, aluminum, tungsten, tantalum, cobalt, nickel, indium, beryllium, brass, iron, platinum, titanium, tungsten carbide, molybdenum oxide, chromium carbide, tantalum carbide, a PGS graphite sheet obtained by graphitizing a polymer film, graphite, carbon nanotube, aluminum nitride, boron nitride, silicon carbide, beryllium oxide, magnesium oxide, and zinc oxide, or a combination thereof.

The ultrasonic transducer may further include a ground sheet formed on the other surface of the active element and electrically connected to the active element.

The present invention also provides a method of manufacturing an ultrasonic transducer, the method including: providing an ultrasonic element having a thickness of ¼ wavelength or less at a center frequency of an ultrasonic signal; and forming a flexible printed circuit board including a metal layer on one surface of the active element, wherein the forming of the flexible printed circuit board comprises increasing a thickness of the metal layer in order to block ultrasonic waves which propagate from the active element in a direction opposite to a direction of a predetermined travel path of the ultrasonic waves.

The forming of the flexible printed circuit board by increasing the thickness of the metal layer may include increasing the thickness to be ⅔ wavelength or more at a center frequency of an ultrasonic signal.

The forming of the flexible printed circuit board by increasing the thickness of the metal layer may include thick-film depositing the metal layer on the surface of the active element.

Advantageous Effects

According to one embodiment, the thickness of a metal layer of a flexible printed circuit board is increased, and thus the interface between the metal layer and an active element acts as a node so that ultrasonic waves which propagate in a direction opposite to a direction of a predetermined travel path of ultrasonic waves are blocked and the ultrasonic waves propagate only in the predetermined travel path of the ultrasonic waves, and thereby the sensitivity and bandwidth of the ultrasonic transducer are improved.

In addition, in order to block the ultrasonic waves that propagate in a direction opposite to a direction of the predetermined travel path of the ultrasonic waves, only a thickness of the metal layer of the flexible printed circuit board is increased without need of adding a de-matching layer between the active element and a backing layer, wherein the de-matching layer has an acoustic impedance value greater than the acoustic impedance value of the active element, and hence the manufacturing method thereof is simple and the manufacturing cost can be reduced.

Moreover, since the thickness of the active element is a length of ¼ wavelength (¼λ) or less based on a center frequency of the active element, the acoustic impedance is reduced and the electrical matching with a system is easy. In this case, a ¼ wavelength transducer may be provided by only increasing the thickness of the metal layer of the flexible printed circuit board.

Also, the flexible printed circuit board having a thick metal layer of the present invention can be applied to any types of transducers, such as an inner array, a convex array, a phased array, a single element, and the like.

Furthermore, since a thick-film deposition method is used when the metal layer of the flexible printed circuit board is formed on one surface of the active element, the thickness of the flexible printed circuit board can be precisely controlled without complicated processes, such as grinding and cutting, which are required in a conventional processing method, such as bonding. In addition, the manufacturing cost is reduced as compared with the processing method.

MODE FOR INVENTION

A preferred embodiment of the present invention will be described herein below with reference to the accompanying drawings. In the following description, well-known functions or constructions are not described in detail since they would obscure the invention in unnecessary detail. The terms used herein are defined in consideration of the functions of elements in the present invention. The terms can be changed according to the intentions or the customs of a user and an operator.

It will be understood that when a first layer is referred to as being "on" or "connected to" a second layer and unless it is explicitly stated that the first layer is "directly on" or "directly connected to" the second layer, the first layer can be directly on or directly connected to the second layer, or a third layer may intervene between the first and second layers.

Figure 1:
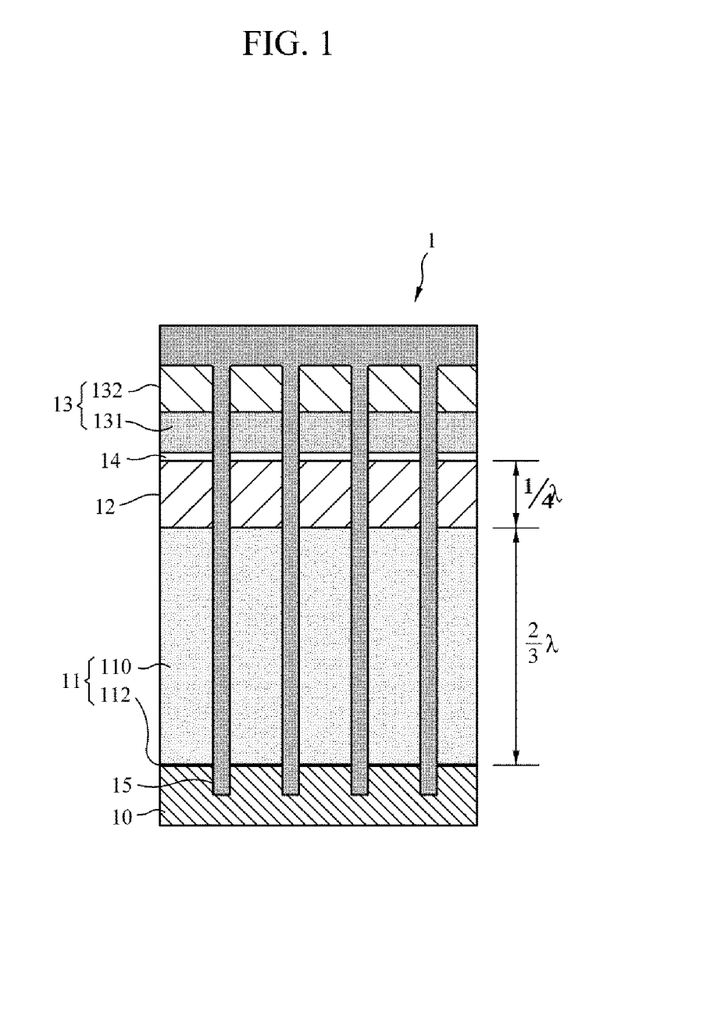
FIG. 1 is a structural view diagrammatically showing a configuration of an ultrasonic transducer having a thick flexible printed circuit board (FPCB) according to one embodiment of the present invention.

FIG. 1 is a structural view diagrammatically showing a configuration of an ultrasonic transducer having a thick flexible printed circuit board according to one embodiment of the present invention.

The term "diagrammatic" used herein means that the shown drawings illustrate relative positional relationships or stacking relationships between elements included in the ultrasonic transducer. Therefore, the specific shape, thickness, etc. of the elements included in the ultrasonic transducer may not necessarily match those shown in the drawings.

Referring to FIG. 1, the ultrasonic transducer 1 includes a backing layer 10, a flexible printed circuit board (FPCB, hereinafter, will be referred to as an "FPCB") 11, an active element 12, a matching layer 13, and a kerf 15, and may further include a ground sheet (GRS, hereinafter, will be referred to as a "GRS") 14.

The ultrasonic transducer 1 may be a single element transducer or an array transducer which consists of a plurality of elements. Types of the array transducer may include a linear array, a convex array, and a phased array, and the present invention may be applicable to all types of array transducer.

The active element 12 generates and transmits an ultrasonic signal to a subject, and receives an ultrasonic signal reflected from the subject, and, for example, a piezoelectric element is used. The backing layer 10 minimizes the returning of the reflective waves of the ultrasonic signal which is generated by the active element 12 and propagates in an undesired direction, i.e., toward the backing layer 10.

Generally, in a transducer, a thickness of an active element has a half wavelength (½λ) length based on the center frequency of an ultrasonic signal generated by the active element. However, in order to enhance the sensitivity and expand the bandwidth of the transducer, the present invention uses the active element 12 having a length of ¼λ, or less based on the center frequency. Since the thickness of the ¼ wavelength active element 12 is reduced by half compared with the thickness of a ½ wavelength active element, acoustic impedance is reduced, the sensitivity is high and the bandwidth is wide.

The efficiency of the transducer is lowered when an ultrasonic signal propagates in both the direction of a predetermined travel path of ultrasonic waves and the direction of the backing layer which is opposite to the direction of the predetermined travel path of ultrasonic waves. In order to block or attenuate the ultrasonic signal propagating in the direction of the backing layer, a de-matching layer may be provided between the active element and the backing layer. The de-matching layer has an acoustic impedance value which is greater than the acoustic impedance value of the active element, for example, at least two times greater than the acoustic impedance value of the active element. In this case, another de-matching layer needs to be additionally provided.

In the ultrasonic transducer 1 according to the present invention, a metal layer 110 of the FPCB 11 having a function of electrical interconnection of the active element 12 is formed to be thick at a lower side of the active element 12 without using an additional de-matching layer, and thus the interface between the metal layer 110 and the active element 12 acts as a node due to the thickness of the metal layer 110, so that the ultrasonic signal is prevented from propagating in a direction opposite to the predetermined ultrasonic propagation path. The active element 12 to which a baffle condition is applied generates an ultrasonic signal by deforming the active element 12, for example, a piezoelectric element, in a direction of a predetermined travel path of ultrasonic waves with respect to the contacting surface between the active element 12 and the metal layer 110, and the ultrasonic signal generated by the active element 12 is blocked from propagating in the direction of the backing layer 10. Therefore, the ultrasonic signal propagates only in the direction of the predetermined travel path of ultrasonic waves, and thereby the sensitivity is improved.

Hereinafter, each element of the ultrasonic transducer 1 having a thick FPCB 11 will be described in detail.

The backing layer 10 is configured such that the acoustic impedance matches the active element 12. The backing layer 10 may be configured to have acoustic attenuation characteristics, which are excellent sound absorption characteristics. The backing layer 10 having the excellent sound absorption characteristics suppresses the free vibration of the active element 12 formed on the front surface to reduce the pulse width of ultrasonic waves and to block the unnecessary propagation of the ultrasonic waves to a rear surface which are generated by the active element 12, thereby effectively preventing the occurrence of image distortion. The backing layer 10 may be formed with a single or a plurality of layers using a material with excellent sound absorption characteristics.

The FPCB 11 according to one embodiment is formed on a rear surface of the active element 12. The metal layer 110 of the FPCB 11 is electrically connected to the active element 12 and applies voltage to the active element 12. In addition, the active element 12 of the metal layer 110 has a thick thickness in order to block the ultrasonic waves propagating in a direction of the backing layer 10. The thickness of the metal layer 110 may be a length of ⅔ wavelength (⅔λ) or more at the center frequency of the ultrasonic signal generated by the active element 12. The thickness of the metal layer 10 may be 50 μm to 50 mm, but is not limited thereto.

The FPCB 11 according to one embodiment consists of a substrate layer 112 and the metal layer 110, and the metal layer 110 is formed on the substrate layer 112. The substrate layer 112 may be polyimide (PI), but is not limited thereto. For the metal layer 110, at least one or more metal raw materials are selected or mixed together to adjust the acoustic impedance and the thermal conductivity. For example, the metal layer 110 may be formed of one of copper, gold, silver, aluminum, tungsten, tantalum, cobalt, nickel, indium, beryllium, brass, iron, platinum, titanium, tungsten carbide, molybdenum oxide, chromium carbide, tantalum carbide, a PGS graphite sheet obtained by graphitizing a polymer film, graphite, carbon nanotube, aluminum nitride, boron nitride, silicon carbide, beryllium oxide, magnesium oxide, and zinc oxide, or a combination thereof. However, the metal layer 110 may be made of any material having conductivity.

The metal layer 110 of the FPCB 11 according to one embodiment may be deposited as a thick film on one surface of the active element 12. In this case, the deposition may be performed such that the thickness of the metal layer 110 becomes a length of ⅔ wavelength or more at the center frequency of the ultrasonic signal. The deposition method for the metal layer 110 will be described with reference to FIG. 4.

The active element 12 according to one embodiment has a length of ¼ wavelength (¼λ) or less based on the center frequency in order to enhance the sensitivity of the transducer and expand the bandwidth. The active element 12 generates an ultrasonic signal when energy is applied thereto by a method, such as applying an electrical signal from the FPCB 11 and the GRS 14 which are located at both ends. The type of the active element 12 may vary depending on the type of the ultrasonic transducer 1, and generally may be formed as a piezoelectric element. The piezoelectric element has the properties that a voltage is generated when a mechanical pressure is applied through a piezoelectric effect and a mechanical deformation occurs when a voltage is applied. The shape or array pattern of the piezoelectric elements is not particularly limited. The piezoelectric element may be formed of a piezoelectric ceramic, such as a lead zirconate titanate (PZT) group, a single crystal, or a composite piezoelectric material in which these materials and a polymer material are combined, a piezoelectric material of a polymer material typified by polyvinylidene fluoride (PVDF), or the like.

The matching layer 13 is disposed between the active element 12 and the subject to mediate the difference in acoustic impedance between the two elements. For example, the matching layer 13 may transfer the ultrasonic waves generated by the active element 12 to the subject or reduce the reflected signal returning from the subject. The matching layer 13 may serve as a buffer to reduce problems, such as image distortion due to a sudden change in acoustic impedance between the active element 12 and the subject.

The matching layer 13 may have a structure in which multiple layers are stacked. For example, as shown in FIG. 1, the matching layer 13 may be composed of a first matching layer 131 and a second matching layer 132, but the number of matching layers is not limited to two. The reason for composing the matching layer 13 with multiple layers is that it is difficult to form the matching layer having a required characteristic with a layer of a single material because the difference in acoustic impedance between the active element 12 and the human tissue, which is the subject, is relatively large.

The GRS 14 may be formed between the matching layer 13 and the active element 12, and the matching layer 13 may exchange an electrical signal with the active element 12 through the GRS 14. The kerf 15 is filled between the elements.

Meanwhile, in FIG. 1, the FPCB 11 is located on the front surface of the backing layer 10 and the GRS 14 is located on the rear surface of the matching layer 13, but the positions thereof may vary depending on the polarization direction of the layer constituting the active element. For example, the GRS 14 may be formed at the position of the FPCB 11 and the FPCB 11 may be formed at the position of the GRS 14.

Figure 2:
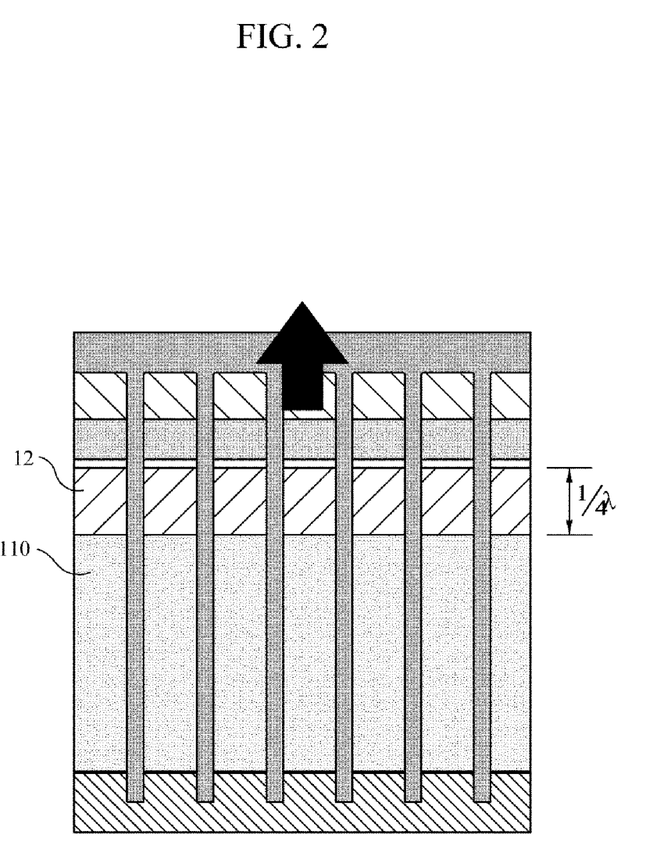
FIG. 2 is a structural diagram of an ultrasonic transducer for describing an ultrasonic signal propagation principle of the ultrasonic transducer including a thin active element and an FPCB having a thick metal layer according to one embodiment of the present invention.

FIG. 2 is a structural diagram of an ultrasonic transducer for describing an ultrasonic signal propagation principle of the ultrasonic transducer including a thin active element and an FPCB having a thick metal layer according to one embodiment of the present invention.

Referring to FIG. 2, in the transducer according to one embodiment, the thickness of the active element is thin and the thickness of the metal layer of the FPCB is thick. For example, the active element 12 has a length of ¼ wavelength (¼λ) or less based on the center frequency of an ultrasonic signal, and the metal layer 110 of the FPCB 11 has a thickness of ⅔ wavelength (⅔λ) or more based on the center frequency of the ultrasonic signal. Accordingly, a baffle condition is satisfied, which blocks the propagation of the ultrasonic signal in a direction opposite to a predetermined travel path of ultrasonic waves. The active element 12 to which the baffle condition is applied generates an ultrasonic signal by deforming the active element 12, for example, a piezoelectric element, in a direction of a predetermined travel path of ultrasonic waves with respect to the contacting surface between the active element 12 and the metal layer 110, and the ultrasonic signal generated by the active element 12 is blocked from propagating in the direction of the backing layer 10. Therefore, the ultrasonic signal propagates only in the direction of the predetermined travel path of ultrasonic waves, and thereby the sensitivity is improved.

Figure 3:
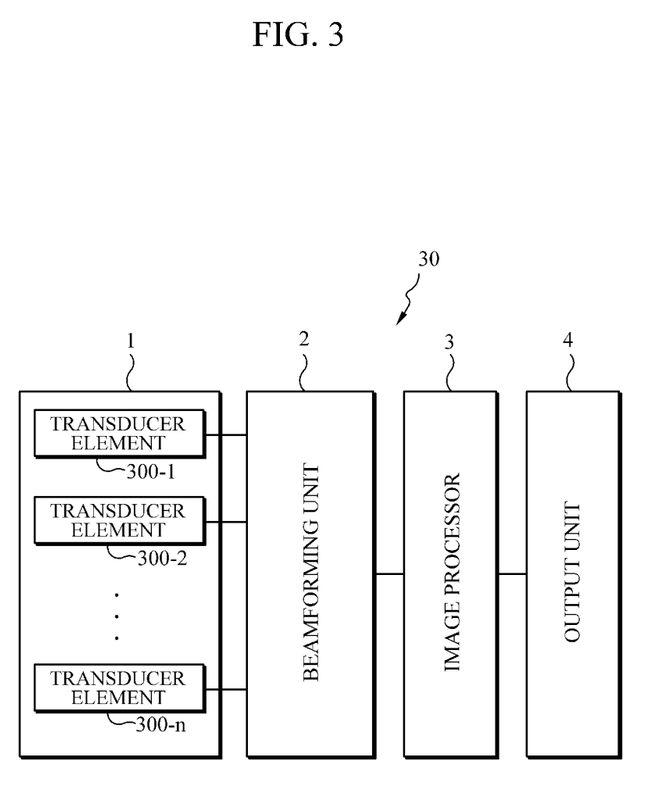
FIG. 3 is a block diagram illustrating an ultrasonic diagnostic apparatus according to one embodiment of the present invention.

FIG. 3 is a block diagram illustrating an ultrasonic diagnostic apparatus according to one embodiment of the present invention.

Referring to FIG. 3, the ultrasonic diagnostic apparatus 30 may include an ultrasonic transducer 1, a beamforming unit 2, an image processor 3, and an output unit 4.

The ultrasonic transducer 1 may be formed with a plurality of transducer elements 300-1, 300-2 to 300-n. According to one embodiment, the ultrasonic transducer 1 includes an active element having a thickness of ¼ wavelength or less at the center frequency of an ultrasonic signal and an FPCB having a thick metal layer on one surface of the active element. The metal layer is electrically connected to the active element to provide an electrical signal to the active element, and has a thickness thick enough to block ultrasonic waves which propagate in a direction opposite to a predetermined travel path of ultrasonic waves. The thickness of the metal layer may be ⅔ wavelength or more at the center frequency of an ultrasonic signal. The metal layer of the FPCB according to one embodiment is deposited as a thick film on one surface of the active element so as to have a thick thickness.

The beamforming unit 2 drives the ultrasonic transducer 1 to transmit an ultrasonic signal to a subject and generates a beam signal by processing a reflected signal returning from the subject. The image processor 3 receives the beam signal from the beamforming unit 2 and generates an ultrasonic image. The output unit 4 displays the ultrasonic image generated by the image processor 3 to the outside.

Figure 4:
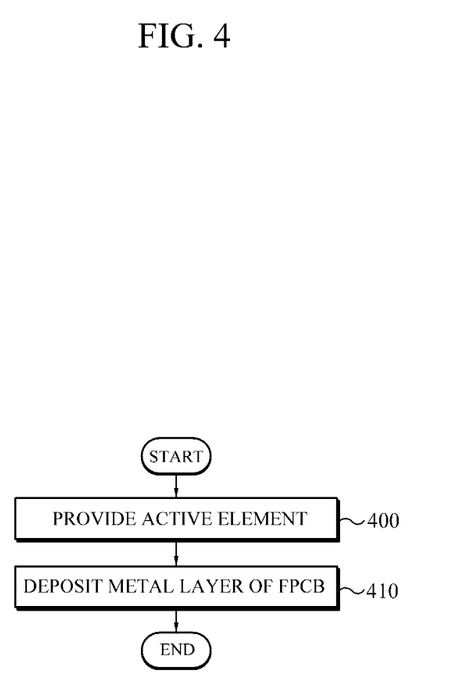
FIG. 4 is a flowchart illustrating a method of manufacturing an ultrasonic transducer according to one embodiment of the present invention.

FIG. 4 is a flowchart illustrating a method of manufacturing an ultrasonic transducer according to one embodiment of the present invention.

Referring to FIG. 4, the method of manufacturing an ultrasonic transducer includes an operation of forming a thick metal layer of an FBCB on one surface of an active element. To this end, the active element having a thickness of ¼ wavelength or less at the center frequency of an ultrasonic signal is provided, as depicted in 400. In addition, the FPCB is formed on one surface, for example, a rear surface of the active element, wherein the thickness of the metal layer formed on the rear surface of the active element is increased. The metal layer is deposited as a thick film so as to have a thick thickness, as depicted in 410. In this case, the deposition may be performed such that the thickness of the metal layer is a length of ⅔ wavelength or more at the center frequency of the ultrasonic signal. The thickness of the FPCB may be precisely controlled without complicated processes, such as grinding and cutting, by using the thick film deposition method of the present invention rather than a conventional processing method, such as bonding. In addition, the manufacturing cost is reduced as compared with the processing method.

Figure 5:
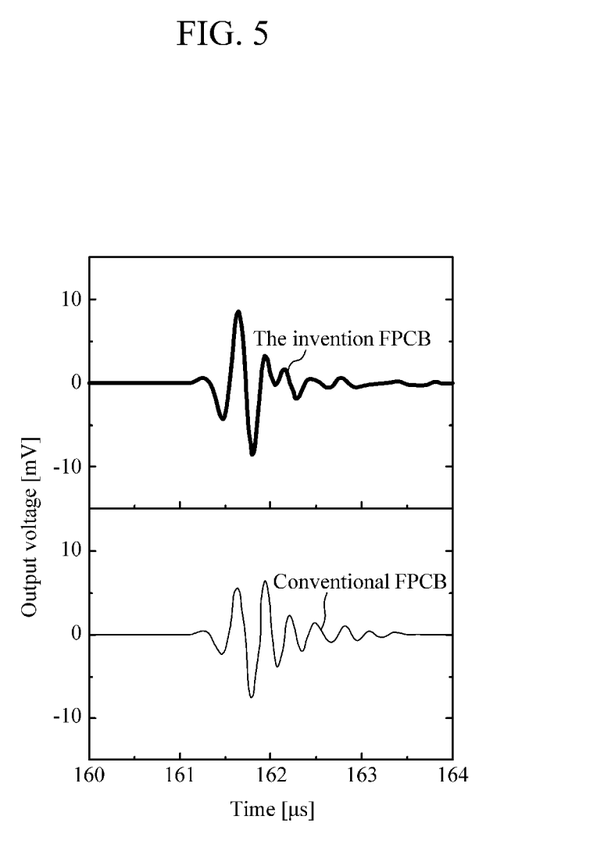
FIGS. 5 to 7 are graphs showing differences in performance between a conventional ultrasonic transducer and an ultrasonic transducer having a thin active element and an FPCB including a thick metal layer according to one embodiment of the present invention.
Figure 6:
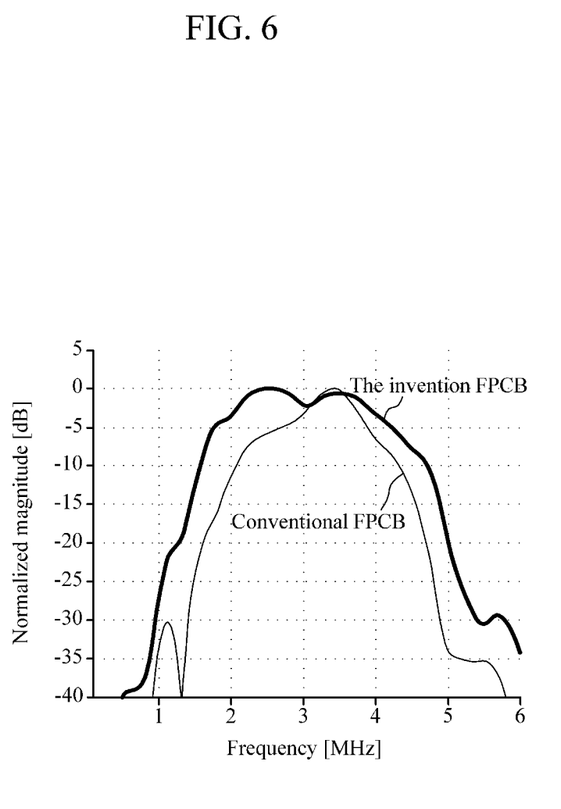
Figure 7:
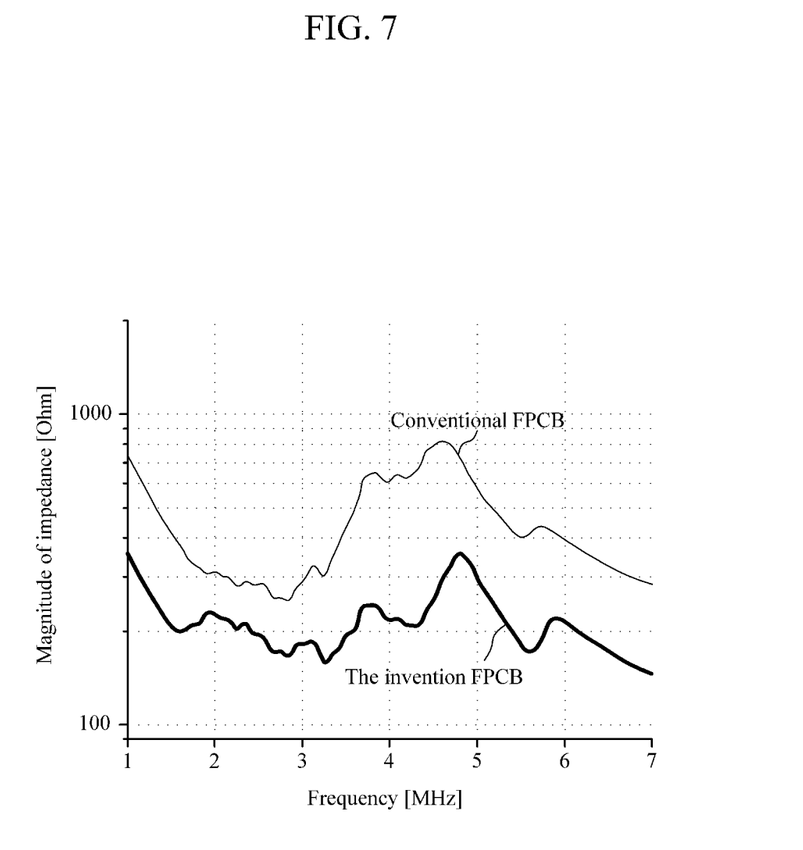

FIGS. 5 to 7 are graphs showing differences in performance between a conventional ultrasonic transducer and an ultrasonic transducer having a thin active element and an FPCB including a thick metal layer according to one embodiment of the present invention.

Referring to FIGS. 5 to 7, it is shown that the sensitivity and bandwidth of the ultrasonic transducer having an FPCB with a thick metal layer are improved.

In detail, FIG. 5 is a graph comparing the magnitude of output voltage of a conventional ultrasonic transducer with respect to time and the magnitude of output voltage of an ultrasonic transducer having an FPCB with a thin active element and a thick metal layer of the present invention. As shown in FIG. 5, it is seen that the ultrasonic transducer of the present invention exhibits a larger voltage change during the same time interval.

FIG. 6 is a graph comparing a normalized magnitude of a conventional ultrasonic transducer with respect to frequency and a normalized magnitude of the ultrasonic transducer having the FPCB with a thin active element and a thick metal layer of the present invention.

Referring to FIG. 6, it is seen that the ultrasonic transducer of the present invention exhibits a larger normalized magnitude in a wider range. Accordingly, the bandwidth of the ultrasonic transducer of the present invention is broadened and the sensitivity thereof is enhanced. In the case of an active element to which a baffle condition is applied, the active element is deformed in an upward direction with respect to the contacting surface between the active element and the metal layer of the FPCB, so that all the ultrasonic waves generated by the active element propagate only in a direction opposite to a direction of a backing material.

FIG. 7 is a graph comparing the magnitude of impedance of a conventional ultrasonic transducer and the magnitude of impedance of the ultrasonic transducer having an FPCB with a thin active element and a thick metal layer of the present invention.

Referring to FIG. 7, it is seen that in the case of the ultrasonic transducer of the present invention, the magnitude of acoustic impedance is reduced due to a reduced active element and the electrical matching with a system is easy.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. An ultrasonic transducer comprising:
an active element configured to generate an ultrasonic signal and having a thickness of ¼ wavelength or less at a center frequency of the generated ultrasonic signal; and
a flexible printed circuit board comprising a metal layer formed on one surface of the active element, electrically connected to the active element and having a predetermined thickness to block ultrasonic waves that propagate in a direction opposite to a predetermined travel path of the ultrasonic waves,
wherein the predetermined thickness of the metal layer is ⅔ wavelength or more at the center frequency of the generated ultrasonic signal.

2. The ultrasonic transducer of claim 1, wherein the metal layer of the flexible printed circuit board is formed on a rear surface of the active element and applies an electrical signal to the active element,
wherein the active element generates the ultrasonic signal by an electrical signal applied from the metal layer and transmits the ultrasonic signal, and
wherein an interface between the metal layer and the active element acts as a node due to the predetermined thickness of the metal layer such that the ultrasonic signal is blocked from propagating in a direction of a backing layer formed on a rear surface of the flexible printed circuit board and the ultrasonic signal propagates only in the direction of the predetermined travel path of ultrasonic waves to increase sensitivity and bandwidth of the ultrasonic transducer.

3. The ultrasonic transducer of claim 1, wherein the metal layer of the flexible printed circuit board is deposited on one surface of the active element to the predetermined thickness.

4. The ultrasonic transducer of claim 3, wherein the metal layer of the flexible printed circuit board is deposited as a thick film.

5. The ultrasonic transducer of claim 1, wherein an acoustic impedance and thermal conductivity of the metal layer are controlled by selecting or mixing at least one or more metal raw materials.

6. The ultrasonic transducer of claim 5, wherein the metal layer is formed of one of copper, gold, silver, aluminum, tungsten, tantalum, cobalt, nickel, indium, beryllium, brass, iron, platinum, titanium, tungsten carbide, molybdenum oxide, chromium carbide, tantalum carbide, a PGS graphite sheet obtained by graphitizing a polymer film, graphite, carbon nanotube, aluminum nitride, boron nitride, silicon carbide, beryllium oxide, magnesium oxide, and zinc oxide, or a combination thereof.

7. The ultrasonic transducer of claim 1, further comprising a ground sheet formed on the other surface of the active element and electrically connected to the active element.

8. A method of manufacturing an ultrasonic transducer, the method comprising:

providing an ultrasonic element having a thickness of ¼ wavelength or less at a center frequency of an ultrasonic signal; and forming a flexible printed circuit board including a metal layer on one surface of the active element, wherein the forming of the flexible printed circuit board comprises increasing a thickness of the metal layer in order to block ultrasonic waves which propagate from the active element in a direction opposite to a direction of a predetermined travel path of the ultrasonic waves, and wherein the forming of the flexible printed circuit board by increasing the thickness of the metal layer comprises increasing the thickness of the metal layer to be ⅔ wavelength or more at the center frequency of the ultrasonic signal.

9. The method of claim 8, wherein the forming of the flexible printed circuit board by increasing the thickness of the metal layer comprises thick-film depositing the metal layer on the surface of the active element.

* * * * *